United States Patent [19]
Pamukcu et al.

[11] Patent Number: 6,037,345
[45] Date of Patent: Mar. 14, 2000

[54] METHOD FOR INHIBITING NEOPLASTIC CELLS AND RELATED CONDITIONS BY EXPOSURE TO QUINAZOLINEDIONE AND PYRIDOPYRIMIDINEDIONE DERIVATIVES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 09/005,731

[22] Filed: Jan. 13, 1998

[51] Int. Cl.⁷ .................................................. A61K 31/505
[52] U.S. Cl. .............................................................. 514/258
[58] Field of Search ............................................. 514/258

[56] References Cited

U.S. PATENT DOCUMENTS 4,880,810  11/1989  Lowe, III ................................ 514/258

*Primary Examiner*—Jerome D. Goldberg
*Attorney, Agent, or Firm*—Robert W. Stevenson

[57] ABSTRACT

This invention relates to a method for the selective inhibition of neoplastic cells, for example, for the treatment of pre-cancerous lesions or other neoplasias in mammals.

6 Claims, No Drawings

METHOD FOR INHIBITING NEOPLASTIC CELLS AND RELATED CONDITIONS BY EXPOSURE TO QUINAZOLINEDIONE AND PYRIDOPYRIMIDINEDIONE DERIVATIVES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds that are useful in the methods of this invention include quinazoline-1H,3H-2,4-diones and pyrido-[2,3d]-pyrimidine-1H,3H-2,4-diones of Formula I

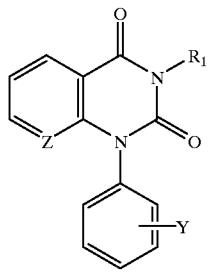

or a pharmaceutically acceptable acid addition salt thereof, wherein $R_1$ is hydrogen, alkyl of 1 to 3 carbon atoms, cyclopentylmethyl, cyclohexylmethyl, norbornylmethyl, [2.2.2]bicyclooctylmethyl, or benzyl, the phenyl of the benzyl optionally being substituted by halogen, trifluoromethyl, nitro, carboxy, or $CO_2M$ wherein M is a pharmaceutically acceptable cation; Y is carboxy, carboalkoxy wherein the alkoxy has 1 to 6 carbon atoms, carbobenzyloxy, carboxamido, N-alkyl carboxamido wherein the alkyl has 1 to 6 carbon atoms, or $CO_2M$ wherein M is defined above, and Z is N or CH, provided that when Z is CH, then $R_1$ is benzyl and Y includes tetrazole optionally substituted by alkyl of 1 to 3 carbon atoms or benzyl.

When Z is N, Y may be substituted in the meta or para position of the 1-phenyl group. When Z is CH, Y is meta-substituted. When $R_1$ is substituted benzyl, the substitution is at the meta and/or para positions.

Preferred compounds that may be useful in the methods of this invention are those wherein $R_1$ is benzyl, Z is N or CH and Y is N-methylcarboxamido or carbomethoxy.

DETAILED DESCRIPTION OF THE INVENTION

As indicated above, this invention relates to a method for inhibiting neoplasia, particularly cancerous and precancerous lesions by exposing the affected cells to a compound of Formula I above.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_3$ are defined as above.

In still another form, the invention is a method of inducing apoptosis in human cells by exposing those cells to an effective amount of compounds of Formula I, to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

Compounds useful in the methods of this invention may be formulated into compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of adminsistation (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

As disclosed in U.S. Pat. No. 4,880,810 the compounds of Formula I wherein $R_1$ is as defined above, except $R_1$ is not benzyl substituted by carboxy, and Y is as defined above may be prepared by reacting, in the presence of an acid catalyst, a compound of the Formula.

wherein X is alkoxy of 1 to 6 carbon atoms and Y1, is Y except for carboxy, with a compound of Formula III.

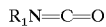

wherein $R_1$ is as defined above except that when $R_1$ is carboxy-substituted benzyl, the carboxy group is a protected group such as an ester group which is subsequently hydrolyzed to release the carboxy group.

The cyclization reaction is conveniently carried out in an organic solvent such as dimethylformamide, diglyme, tetrahydrofaran or alcohol, in the presence of an acid catalyst such as hydrogen chloride. The reaction temperature is not critical, and may be ambient or higher, e.g. up to about 200° C. However, preferably, the reaction is at the reflux temperature of the solvent used.

The carboxylic acid (I) wherein Y is carboxy may be prepared from corresponding compounds wherein Y is carboalkoxy by conventional hydrolysis such as in ethanolic base. The base may be potassium hydroxide.

The compound (I) wherein $R_1$ is benzyl substituted by carboxy is prepared from the corresponding compound (I) wherein $R_1$ as a protected group such as a carboalkoxy, wherein the alkoxy has 1 to 6 carbon atoms, by conventional hydrolysis as described above.

The compound (I) wherein Y is carbobenzyloxy may be prepared by transesterification of compound (I) wherein Y is carboalkoxy with benzylalcohol in the presence of a catalyst such as an acid or base.

The amide (I) wherein Y is carboxamido or N-alkylcarboxamido may be prepared by reacting the corresponding carboxylic acid (I) with ammonia or an alkylamine, respectively, wherein the alkyl in the alkylamine contains from 1 to 6 carbon atoms.

The compounds of Formula II are prepared by recting 2-chloronicotinic acid with 3-aminobenzoic acid in an inert atmosphere such as nitrogen. The reaction is usually carried out in an organic solvent such as dimethyl formamide, diglyme, tetrahydrofuran or an alcohol. Preferably, a metallic compound is present such as copper powder or copper bromide, and an inorganic base such as alkali metal carbonate or hydroxide, or an organic base such as trialkylamine, or pyridine. The reaction temperature is not critical and may be ambient or elevated up to about 150° C. Preferably, the reaction is carried out at the reflux temperature of the organic solvent used.

The isocyanate $R_1N=C=O$ wherein $R_1$ is as defined above in connection with Formula I except that $R_1$ is not benzyl substituted by carboxy may be formed by reaction of diphenylphosphoryl azide with a compound of formula $R_1COOH$, wherein $R_1$ is as defined immediately above in connection with $R_1NCO$, in the presence of a weak base such as a tertiary amine, e.g. triethylamine.

The formation of the isocyanate is preferably done in situ without isolation of the isocyanate before the subsequent cyclization to compounds of formula I as described above. The solvents for the in situ formation of the isocyanate and the subsequent cyclization must be inert under the reaction conditions of both the isocyanate formation and the cyclization. Suitable solvents are higher boiling hydrocarbons, such as xylene or chlorobenzene having boiling points of about 130° to 140°, and other organic solvents such as dimethylformamide, and diglyme.

Alternative general methods which can be adapted to make novel compounds (I) are described in the prior art such as above mentioned U.S. Pat. No. 3,984,415, the disclosure of which is hereby incorporated by reference, and British Patent 1,484,293.

The pharmaceutically acceptable cation salts of the compounds of Formula I may be prepared by conventional methods. For instance, the salts may be prepared by treating the compound of Formula I in which $R_1$ is carboxybenzyl or Y is carboxy with an aqueous solution of the desired pharmaceutically acceptable cation in the hydroxide form in equivalent amounts, and evaporating the resulting solution to dryness, preferably under reduced pressure. Suitable pharmaceutically acceptable cation hydroxides for this purpose include alkali metal hydroxides such as potassium, sodium and lithium hydroxides, alkaline earth metal hydroxides such as calcium and magnesium hydroxide. Alternatively, the salts may be prepared by reaction of compound (I) in which Y is carboxy with ammonia or organic amines, such as diethanolamine and N-methylflucamine.

The pharmaceutically acceptable acid addition salts of the compounds of Formula I wherein Z is N are prepared in a conventional manner by treating a solution or suspension of the free base (I) with about one chemical equivalent of a pharmaceutically acceptable acid. Conventional concentration and recrystallization techniques are employed in isolating the salts. Illustratives of suitable acids are sulfuric, phosphoric, hydrochloric, hydrobromic, hydroiodic, sulfamic, sulfonic such as methanesulfonic, benzenesulfonic, tribluoromethanesulfonic and related acids. Preferably, the acid is methanesulfonic acid.

The compounds useful in this invention may be administered at dosage levels of about 0.1 to 30 mg/kg/day, advantageously 0.5–20 mg/kg/day. Variations will necessarily occur depending on the weight and condition of the subject being treated and the particular route of administration chosen as will be known to those skilled in the art The following Examples illustrate the invention. All temperatures are in degrees centigrade.

EXAMPLE 1

1-(3-carboxymethoxyphenyl)3-Benzyl-Pyrido-[2,3d] Pyrimidine-1H,3H-2,4-Dione (A) Methyl 2-(3-carbomethoxphenylamino)-nicotinate To a 500 ml round-bottomed flask equipped with condenser and $N_2$ inlet are added 15.7 g (0.10 mol) of 2-chloronicotinic acid, 19.9 g (0.145 mol) of 3-aminobenzoic acid, 34.5 g (0.25 mol) of potassium carbonate, 30 mg of copper powder, and 40 ml of dimethylformamide. The mixture is heated to reflux and 150 mg of methanol-washed copper(I) bromide is added in three portions over 10 minutes. The reaction turns dark and partially solidifies as it is refluxed for 4.5 hours. It is then cooled, taken up in 1 liter 1N HCl, the pH adjusted to 3.5, and filtered to remove copper and dark, tarry impurities. The filtrate is adjusted to pH 2.5, saturated with sodium chloride, stirred for 3 hours, and the precipitate filtered, washed with a minimal amount of water, and dried.

The resulting solid is taken up in 500 ml dry methanol, saturated with hydrogen chloride gas, and heated at reflux for 2.5 days. The reaction is cooled, filtered from some residual sodium chloride from the previous step, and evaporated. The residue is taken up in excess aqueous saturated sodium bicarbonate solution, stirred and the aqueous layer decanted off the resulting gummy precipitate. The precipitate is chromatogrphed on silica gel using 5% ethyl acetate in methylene chloride as eluent to afford a light yellow oil, which crystallizs on standing, mp 105°–106° C.

(B) 1-(3-Carbomethoxyphenyl)-3-benzyl-pyrido-[2,3d]-pyrimidine-1H,3H-2,4-dione

To a 65 ml round-bottomed flask equipped with condenser and $N_2$ inlet are added 2.22 g (7.76 mmol) of methyl 2-(3-carbomethoxyphenylamino)-nicotinate, 3 ml dry xylene, 0.96 ml (7.76 mmol) of benzyl isocyanate, and 3 mg of camphorsulfonic acid. The reaction is heated to reflux for 6 days, cooled, evaporated, and the residue is chromatographed on silica agel using 3% ethyl acetate in methylene chloride to elute unreacted diester and 10% ethyl acetate in methylene chloride to elute the product, which is triturated with ether to a white solid, mp 157°–160° C., 938 mg (31.2% yield).

EXAMPLE 2

1-(3-Benzyloxycarbonylphenyl)-3-Benzyl-Pyrido-[2, 3d]-Pyrimidine-1H,3H-2,4-Dione To a 35 ml round-bottomed flask equipped with condenser and $N_2$ inlet are added 0.30 g (0.77 mmol) of 1-(3-methoxycarbonylphenyl)-3-benzyl-pyrido-[2,3d]-pyrimidine-1H,3H-2,4-dione, 8 ml of benzyl alcohol, and 10 mg of camphorsulfonic acid. The reaction is heated at reflux for 48 hours, cooled, and chromaatographed on silica gel using ether/hexane. The product fractions are combined and triturated with ether to give 32 mg (9.0% yield) of white crystalline solid, mp 160°–162° C.

EXAMPLE 3

1-(3-Carboxyphenyl)-3-Benzyl-Pyrido-[2,3d]-Pyrimidine-1H,3H-2,4-Dione

To a 35 ml round-bottomed flask equipped with condenser and $N_2$ inlet are added 100 mg (0.26 mmol) of 1-(3-carbomethoxyphenyl)-3-benzyl-pyrido-[2,3d]-pyrimidine-1H,3H-2,4-dione, 15 mg (0.26 mmol) of sodium chloride, 9 mg (0.52 mmol) of water, and 1.5 ml of dimethylsulfoxide. The reaction is heated at reflux for 3 days, cooled, diluted with water, and extracted into ethyl acetate. The organic layer is dried over magnesium sulfate, filtered, and evaporated. The resulting oil is chromatographed on silica gel using methylene chloride/methanol as eluent, and product fractions combined and evaporated. The resulting solid is triturated with pentane/ethyl ether to afford an off-white solid, mp 248°–250° C., 4 mg.

EXAMPLE 4

1-(3-Carboethoxyphenyl)-3-Benzyl-Pyrido-[2,3d]-Pyrimidine-1H,3H-2,4-Dione

To a 35 ml round-bottomed flask equipped with condenser and $N_2$ inlet are added 600 mg (1.91 mmol) of ethyl 2-(3-carboethoxyphenlyamino)nicotinate (prepared as in Example 1A but using ethanol in place of methanol), 1 ml dry dimethylformamide, 0.25 g (1.91 mmol) of benzyl isocyanate, and 10 mg camphosulfonic acid. The reaction is heated at reflux for 24 hours, cooled, taken up in ethyl acetate, washed with water, dried over magnesium sulfate, and evaporated to an oil. The oil is chromatographed on silica gel using ethyl acetate/methylene chloride as eluent to give a white crystalline solid, mp 171°–174° C., 70 mg.

EXAMPLE 5

1-(3-Carboisopropyoxyphenyl)-3-Benzyl-Pyrido-[2, 3d]-Pyrimidine-1H,3H-2,4-Dione

To a 35 ml round-bottomed flask eqipped with condenser and $N_2$ inlet are added 690 mg (2.02 mmol) of ethyl 2-(3-carboisopropoxyphenylamino)nicotinate (prepared as in Example 1A but using isopropanol in place of methanol), 1 ml dry dimethylformamide, 0.27 g (2.02 mmol) of benzyl isocyanate, and 10 mg camphorsulfonic acid. The reaction is heated at reflux for 24 hours, cooled, taken up in ethyl acetate, washed with water, dried over magnesium sulfate, and evaporated to an oil. The oil is chromatographed on silica agel using ethyl acetate/methylene chloride as eluent to give a white crystalline solid, mp 205°–207° C., 79 mg.

EXAMPLE 6

1-(3-Carbomethoxyphenyl-3-(4-Fluoro-Benzyl)-Pyrido-[2,3d]-Pyrimidine-1H,3H-2,4-Dione To a 35 ml round-bottomed flask equipped with condenser and $N_2$ inlet are added 1.0 g (3.496 mmol) of methyl 2-(3-carbomethoxyphenylamino)-nicotinate, 0.54 g (3.496 mmol) of 4-fluorophenyl acetic acid, 4 ml of dry xylene, 0.83 ml (3.846 mmol) of diphenylphosphoryl azide, and 0.54 ml (3.846 mmol) of triethyl amine. The reaction is heated to 70° C., whereupon a gas is evolved, and 5 mg camphorsulfonic acid is added once gas evolution has ceased. The reaction is heated at reflux for 2.5 days, cooled, and chromatographed on silica gel using ethyl acetate in methylene chloride as eluent to give 70 mg (4.9% yield) of a white solid, mp 172°–175° C.

EXAMPLE 7

1-(3-Carbomethoxphenyl)-3-(4-Chloro-Benzyl)-Pyrido-[2,3d]-Pyrimidine-1H,3H-2,4-Dione To a 35 ml round-bottomed flask equipped with condenser and $N_2$ inlet are added 1.0 g (3.496 mmol) of methyl 2-(3-carbomethoxyphenylamino)-nicotinate, 0.60 g (3.496 mmol) of 4-fluorophpenyl acetic acid, 4 ml of dry xylene, 0.83 ml (3.846 mmol) of diphenylphosphoryl azide, and 0.54 ml (3.846 mmol) of triethyl amine. The reaction is heated to 70° C., whereupon a gas is evolved, and 5 mg camphorsulfonic acid is added once gas evolution has ceased. The reaction is heated at reflux for 2.5 days, cooled, and chromatographed on silica gel using ethyl acetate in methylene chloride as eluent to give 32 mg (2.2% yield) of a white solid, mp 120°–130° C. NMR (DMSO-d6): 3.87 (3H, s), 5.15 (2H, s), 7.1–8.5 (11H, m).

EXAMPLE 8

1-(3-Carbomethoxphenyl)-3-(Cyclopentylmethyl)-Pyrido-[2,3d]-Pyrimidine-1H,3H-2,4-Dione To a 35 ml round-bottomed flask equipped with condenser and $N_2$ inlet are added 1.0 g (3.496 mmol) of methyl 2-(3-carbomethoxyphenylamino)-nicotinate, 0.44 g (3.496 mmol) of cyclopentyl acetic acid, 4 ml of dry xylene, 0.83 ml (3.846 mmol) of diphenylphosphoryl azide, and 0.54 ml (3.846 mmol) of triethyl amine. The reaction is heated to 70° C., whereupon a gas is evolved, and 5 mg camphorsulfonic acid is added once gas evolution has ceased. The reaction is heated at reflux for 2.5 days, cooled, and chromatogrphed on silica gel using ethyl acetate in methylene chloride as eluent to give 67 mg (5.1% yield) of a white solid, mp 149°–151° C.

EXAMPLE 9

1-(3-Carbomethoxphenyl)-3-(Norbornylmethyl)-Pyrido-[2,3d]-Pyrimidine-1H,3H-2,4-Dione The title compound (281 mg of white solid, mp 157°–159° C.) is prepared as in Example 8 from 1.0 g (3.496 mmol) of methyl 2-(3-carbomethoxyphenylamino)-nicotinate, 0.51 g (3.496 mmol) of norbornyl acetic acid, 4 ml of dry xylene, 0.83 ml (3.846 mmol) of diphenylphosphoryl azide, and 0.54 ml (3.846 mmol) of triethyl amine.

EXAMPLE 10

Methyl 2-(4-Carbomethoxphenylamino)-Nicotinate (A) The title compound (4.8 g white solid, mp 138°–139° C.) is prepared as in Example 1.A from 7.85 g (0.05 mol) of 2-chloronicotinic acid, 9.95 g (0.0725 mol) of 4-aminobenzoic acid, 17.25 g (0.125 mol) of potassium carbonate, 30 mg of copper powder, and 30 ml of dimethylformamide.

1-(4-Carbomethoxyphenyl-3-Benzyl Pyrido-[2,3d]-Pyrimidine-1H,3H-2,4-Dione (B) The title compound (582 mg white solid, mp 179°–181° C.) is prepared as in Example 1.B from 2.22 g (7.76 mmol) of methyl 2-(4-carbomethoxphenylamino)-nicotinate, 3 ml dry xylene, 0.96 ml (7.76 mmol) of benzyl isocyanate, and 3 mg of camphorsulfonic acid.

EXAMPLE 11

1-(3-Carboxamidopphenyl)-3-Benzyl-Pyrido-[2,3d]-Pyrimidine-1H,3H-2,4-Dione

To a 25 ml round-bottomed flask equipped with $N_2$ inlet and rubber septum are added 150 mg (0.402 mmol) of 1-(3-carboxyphenyl)-3-benzyl-pyrido-[2,3d]-pyrimidine-1H,3H-2,4-dione, 1.4 ml methylene chloride, 0.4 ml dimethylformamide, and 41 mg (0.402 mmol) of N-methyl morpholine. The reaction is cooled to –5° C. and 55 mg (0.402 mmol) of isobutylchloroformate is added, and the reaction stirred for 5 minutes. Ammonia gas is then bubbled through the reaction for 3 minutes and the reaction allowed to warm to room temperature and stirred for 2 hours. The reaction is then quenched by addition of 2N aqueous sodium hydroxide solution, and extracted into ethyl acetate. The ethyl acetate layer is washed with 2N aqueous sodium hydroxide and water, dried over magnesium sulfate, and evaporated. The residue is triturated with ether to yield a white solid, 105 mg (70% yield), mp 245°–246° C.

EXAMPLE 12

1-(3-N-Methylccarboxamidophenyl)-3-Benzyl-Pyrido-[2,3d]-Pyrimidine-1H,3H-2,4-Dione To a 25 ml round-bottomed flask equipped with $N_2$ inlet and rubber septum are added 150 mg (0.402 mmol) of 1-(3-carboxphenyl)-3-benzyl—pyrido-[2,3d]-pyrimidine-1H,3H-2,4-dione, 3.0 ml methylene chloride, 0.7 ml dimethylformamide, and 41 mg (0.402 mmol) of N-methyl morpholine. The reaction is cooled to –10° C. and 55 mg (0.402 mmol) of isobutylchloroformate is added, and the reaction stirred for 5 minutes. N-Methylamine gas is then bubbled through the reaction for 2 minutes and the reaction allowed to warm to room temperature and stirred for 2 hours. The reaction is then quenched by addition of 2N aqueous sodium hydroxide solution, and extracted into ethyl acetate. The ethyl acetate layer is washed with 2N aqueous sodium hydroxide and water, dried over magnesium sulfate, and evaporated. The residue is triturated with ether to yield a white solid, 100 mg (64.5% yield), mp 252°–253° C.

EXAMPLE 13

A. Methyl 2-(3-Carbomethoxyphenylamino)-Benzoate

To a 500 ml round-buttomed flask equipped with condenser and $N_2$ inlet are added 15.7 g (0.10 mol)

2-chlorobenzoic acid, 23.3 g (0.17 mol) 3-aminobenzoic acid, 23.5 g (0.17 mol) potassium carbonate, 50 mg copper powder, and 40 ml dimethylformamide. The mixture is heated to reflux, and three 50 mg portions of methanol-washed copper #(I) bromide are added. The reaction is refluxed 3.5 hours, cooled, and poured into 1 1 1N HCl. The mixture is stirred for 10 minutes, filtered, and the filtered solid washed with water, methanol, and ether, and dried to afford a gray solid, mp 277°–279° C., 19 g (73.9%). The acid is taken up in 250 ml methanol, the solution is saturated with HCl and refluxed 40 hours, and cooled and evaporated. The residue is chromatographed on silica gel using methylene chloride as eluent to afford 17.46 g (61.3% overall) of a yellow oil. NMR (d, CDC13): 3.97 (s, 3H), 6.7–8.0 (m, 8H). IR (Cm.$^{-1}$, KBr): 1730 (C=O).

B. 1-(3-Carbomethoxyphenyl)-3-benzylquinazoline-1H, 3H-2,4-dione

To a 250 ml round-bottomed flask equipped with condenser and $N_2$ inlet are added 17.46 g (61.26 mmol) methyl 2-(3-carbomethoxyphenylamino)-benzoate, 2.57 ml (61.26 mol) benzylisocyanate, 5 mg camphorsulfonic acid, and 40 ml xylene. The reaction is refluxed for 3 days, cooled, and evaporated. The residue is crystallized from ethyl acetate/isopropyl ether in two crops to afford a solid, mp 150°–151.5°, 8.80 g (37.2%).

EXAMPLE 14

1-(3-Carboxyphenyl)-3-Benzylquinazoline-1H,3H-2, 4-Dione

To a 500 ml round-bottomed flask equipped with condenser and $N_2$ inlet are added 3.86 g (10 mmol) 1-(3-carbomethoxyphenyl)-3-benzylquinazoline-1H,3H-2,4-dione, 24.1 g (180 mmol) lithium iodide, and 250 ml dimethylformamide. The reaction is refluxed 36 hours cooled, and added to 1 1 1N HCl. The mixture is stirred for 20 minutes, filtered, and the solid washed with water and dried to afford mp 260°–262° C., 3.55 g (95.4%).

EXAMPLE 15

1-(3-N-Methylcarboxamidophenyl)-3-Benzylquinazoline-1H,3H-2,4-Dione

To a 100 ml three-necked round-bottom flask equipped with septum and $N_2$ inlet added 0.50 g (1.34 mnmol) 1-(3-carboxyphenyl)-3-benzylquinazoline-1H,3H-2,4-dione, 0.15 ml (1.34 mmol) N-methylmorpholine, 10 ml methylene chloride, and 1.5 ml dimehylformamide. The solution s cooled to −10° C. and 0.17 ml (1.34 mmol) isobutyl chloroformate added. The reaction is stirred at −10° C. for 10 minutes, then methylamine gas is bubbled through the solution for 10 minutes. The reaction is allowed to warm to room temperature and is stirred for 3 days. It is taken up in methylelne chloride, washed with 1N HCl and brine, dried, and evaporated. The residue is chromatographed on silica gel usiing methylelne chloride/ethyl acetate as eluent to afford 0.45 g (87.2%) of a white, crystalline solid after trituration with isopropyl ether, mp 250°–251° C.

EXAMPLE 16

1-(3-(1-Methyltetrazol-3-yl)Phenyl)-3-Benzylquinazoline-1H,3H-2,4-Dione
(A) 3-(1-Methyltetrazol-3-yl)aniline
To a 125 ml round-bottomed flask equipped with condenser and $N_2$ inlet are added 1.48 g (10 mmol) 3-nitrobenzonitrile, 0.053 g (1 mmol) ammonium chloride, 0.715 g (11 mmol) sodium azide, and 20 ml dimethylformamide. The reaction is heated to 100° C. for 3 hours, cooled, and evaporated. The residue is taken up in water, cooled to 0° C., and adjusted to pH 2 with 6N HCl. The precipitate is filtered and dried to a yellow solid, mp 90°–93° C., 1.5 g (78.5%).

The tetrazole is methylated as follows: To a 125 ml round-bottomed flask equipped with condenser and $N_2$ inlet is added 1.4 g (73.2 mmol) 3-(tetrazol-3-yl)-nitrobenzene, 0.776 g (73.2 mmol) potassium carbonate, 0.455 ml (73.2 mmol) methyl iodide, and 30 ml acetone. The reaction is refluxed for 18 hours, cooled and evaporated. The residue is partitioned between water (adjusted to pH 2) and methylene chloride, the layers separated, and the aqueous layer extracted with methylene chloride. The combined organic layers are dried over sodium sulfate and evaporated. The residue is chromatographed on silica gel using methylene chloride as eluent to afford 0.85 g (56.6%) of a yellow solid, mp 99°–101° C.

The nitro group is reduced as follows: To a 250 ml Parr bottle are added 800 mg (3.9 mmol) of 3-(1-methyltetrazol-3-yl)nitrobenzene, 200 mg platinum oxide, and 75 ml ethanol. The reaction is pressurized with 45 p.s.i. hydrogen for 1 hour, then catalyst removed by filtration, and the solvent evaporated to afford 635 mg (93.0%) of a white solid, mp 93°–95° C.

(B) Methyl 2-(3-(1-methyltetrazol-3-yl)phenylamino)-benzoate

To a 125 ml round-bottomed flask equipped with condenser and $N_2$ inlet are added 2.5 g (14.27 mmol) 3-3-methyltetrazol-3-yl)aniline, 2.23 g (14.27 mmol) 2-chlorobenzoic acid, 4.9 c (35.6 mmol) potassium carbonate, 20 mg copper powder, and 20 ml dimethylformamide. The reaction is heated to reflux and 100 mg of methanol-washed copper (I) bromide is added in four portions over 20 minutes. The reaction is refluxed for 16 hours, cooled, and poured into 200 ml ice/water. The mixture is filtered, washed with methylene chloride. Thi second organic extract is evaporated to afford 800 mg (19.0%) of a slid, mp 197°–199° C.

The solid os dissolved in 50 ml methanol in a 125 ml round-bottomed flask equipped with condenser and $N_2$ inlet and the solution saturated with HCl gas and refluxed for 2 days. The reaction is evaporated and chromatographed on silica gel using ethyl acetate as eluent to afford 500 mg (59.7%) of a yellow solid, mp 106°–108° C.

(C). 1-(3-(1-Methyltetrazol-3-yl)phenyl)-3-benzylquinazoline-1H,3H-2,4-dione To a 10 ml round-bottomed flask equipped with condenser and $N_2$ inlet are added 500 mg (1.61 mmol) methyl 2-(3-(1-methyltetrazol-3-yl)phenylamino)-benzoate, 0.199 ml (1.61 mmol) benzyl isocyanate, 5 mg camphorsulfonic acid, and 2 ml xylene. The reaction is refluxed for 3 days, cooled, and evaporated. The residue is chromatographed on silica gel using methylene chloride/ethyl acetate as eluent to afford 175 mg (26.5%) of a white solid, mp 234°–236° C.

We claim:

1. A method of treating a mammal sensitive to such a compound having precancerous lesions comprising administering to said mammal a pharmacologically effective amount of a compound of Formula I or pharmaceutically acceptable salt thereof:

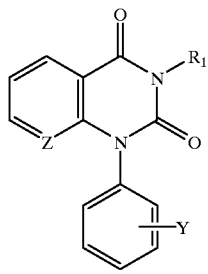

wherein $R_1$ is hydrogen, alkyl of 1 to 3 carbon atoms, cyclopentyllmethyl, cyclohexylmethyl, norbornylmethyl, bicyclooctylmethyl, or benzyl, the phenyl of the benzyl optionally being substituted by halogen, trifluoromethyl, nitro, carboxy, or $CO_2M$ wherein M is a pharmaceutically acceptable cation; Y is carboxy, carboalkoxy;

wherein the alkoxy has 1 to 6 carbon atoms, carbobenzyloxy, carbamoyl N-alkylcarbamoyl wherein the alkyl has 1 to 6 carbon atoms, or $CO_2M$ wherein M is as defined above, and Z is N.

2. The method according to claim 1 wherein $R_1$ is benzyl, and Y is N-methylcarbamoyl.

3. The method according to claim 1 wherein $R_1$ is benzyl, and Y is carbomethoxy.

4. A method for inhibiting the growth of neoplastic cells comprising exposing the cells sensitive to such a compound to a growth inhibiting effective amount of a compound of Formula I or pharmaceutically acceptable salt thereof:

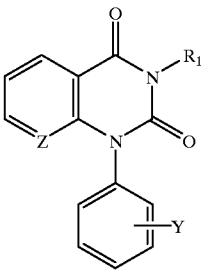

wherein $R_1$ is hydrogen, alkyl of 1 to 3 carbon atoms, cyclopentyllmethyl, cyclohexylmethyl, norbornylmethyl, bicyclooctylmethyl, or benzyl, the phenyl of the benzyl optionally being substituted by halogen, trifluoromethyl, nitro, carboxy, or $CO_2M$ wherein M is a pharmaceutically acceptable cation; Y is carboxy, carboalkoxy wherein the alkoxy has 1 to 6 carbon atoms, carbobenzyloxy, carbamoyl N-alkylcarbamoyl wherein the alkyl has 1 to 6 carbon atoms, or $CO_2M$ wherein M is as defined above, and Z is N.

5. The method according to claim 4 wherein $R_1$ is benzyl, and Y is N-methylcarbamoyl.

6. The method according to claim 4 wherein $R_1$ is benzyl, and Y is carbomethoxy.

* * * * *